United States Patent
Tsuang et al.

(10) Patent No.: US 9,615,855 B2
(45) Date of Patent: Apr. 11, 2017

(54) BONE SCREW AND PERCUTANEOUS MINIMALLY INVASIVE PEDICLE FIXATION SYSTEM

(71) Applicant: Baui Biotech Co., Ltd., New Taipei (TW)

(72) Inventors: Fon Yih Tsuang, New Taipei (TW); Chia Hsien Chen, New Taipei (TW); Chang Jung Chiang, New Taipei (TW); Yi Jie Kuo, New Taipei (TW)

(73) Assignee: BAUI BIOTECH CO., LTD., New Taipei (TW)

( * ) Notice: Subject to any disclaimer, the term of this patent is extended or adjusted under 35 U.S.C. 154(b) by 19 days.

(21) Appl. No.: 14/713,334

(22) Filed: May 15, 2015

(65) Prior Publication Data

US 2016/0331410 A1 Nov. 17, 2016

(51) Int. Cl.
*A61B 17/70* (2006.01)
*A61B 17/68* (2006.01)

(52) U.S. Cl.
CPC ........ *A61B 17/685* (2013.01); *A61B 17/7067* (2013.01); *A61B 2017/681* (2013.01)

(58) Field of Classification Search
USPC ...................................................... 606/261
See application file for complete search history.

(56) References Cited

U.S. PATENT DOCUMENTS

| | | | | |
|---|---|---|---|---|
| 2008/0119849 A1* | 5/2008 | Beardsley | .......... | A61B 17/7032 606/306 |
| 2008/0154280 A1* | 6/2008 | Schumacher | ........ | A61B 17/708 606/104 |
| 2008/0255619 A1* | 10/2008 | Schneiderman | ... | A61B 17/7007 606/276 |
| 2010/0094344 A1* | 4/2010 | Trieu | ................. | A61B 17/7011 606/246 |
| 2010/0274291 A1* | 10/2010 | McClellan, III | ... | A61B 17/7004 606/276 |
| 2011/0263945 A1* | 10/2011 | Peterson | ............ | A61B 17/7074 600/213 |
| 2013/0172937 A1* | 7/2013 | Davenport | ......... | A61B 17/7032 606/278 |
| 2016/0008034 A1* | 1/2016 | Stokes | ............... | A61B 17/7085 606/278 |

* cited by examiner

*Primary Examiner* — Jan Christopher Merene
(74) *Attorney, Agent, or Firm* — Juan Carlos A. Marquez; Marquez IP Law Office, PLLC

(57) ABSTRACT

The percutaneous minimally invasive pedicle fixation system herein comprises a bone screw and a hook-rod, wherein the bone screw includes a positioning casing and a screw body. The positioning casing comprises securing base, an alignment casing and a screw body passage. The securing base includes a through hole at the bottom and two openings arranged opposite to each other in the wall. The alignment casing has a wall portion and a volume reduce portion, wherein the wall portion is configured with an elongate opening and the volume reduced portion is a portion with part of the wall removed to recede from the outer surface of the securing base and a guide opening formed in the volume reduced portion. The positioning casing further includes a first easy breaking portion between the alignment casing and the securing base so that the alignment casing can be removed from the positioning casing.

8 Claims, 16 Drawing Sheets

BONE SCREW AND PERCUTANEOUS MINIMALLY INVASIVE PEDICLE FIXATION SYSTEM

BACKGROUND OF THE INVENTION

1. Field of the Invention

The invention relates to a bone screw and a bone screw fixation system, especially to a bone screw fixation system applicable in percutaneous invasive vertebrae treatment.

2. Description of the Related Art

Minimally invasive surgeries of fixation systems are used in treating vertebrae. Since the wounds are small, such surgeries can largely reduce the damage to the portions under treatment and the neighboring tissues, can enhance the safety of surgeries, and can decrease healing and recovery time. For accurate positioning and alignment of the fixation system, a bone screw of the fixation system is typically provided with a positioning casing. Thus, the bone screw of the fixation system can be positioned and aligned from the outside of a human body while performing the surgery.

The conventional bone screw fixation system needs a separate aligning device to align the bone screw during insertion of the bone screw into bone. The separate aligning device is rather complicated and/or has multiple components, which results in inconvenience and even requires a wound with a larger width or length during operation. Therefore, there is a need to develop a rather simple and convenient bone screw fixation system. Further, more than one bone screw is inserted into a patient's vertebrae. A bone screw fixation system that reduces the number of operation steps and/or operation time is also desirable.

SUMMARY OF THE INVENTION

The invention can improve the efficiency and accuracy of installing a fixation device during invasive vertebrae surgery. For a percutaneous invasive vertebrae surgery, it is preferable to reduce the area or size of wounds caused by the surgery. The fixation system of the preferred invention includes a long tubular structure that helps to align a bone screw during insertion into the vertebrae. The long tubular structure can be an alignment casing in a cylindrical shape with a passage for the bone screw to pass through and integrally form with the base which will be inserted by the bone screw and secured to the bone. The structure can then be removed after the implantation process has finished. When more than one bone screw is needed to be implanted neighboring one another, it is preferred that the diameter of the enclosed tubular structure of the fixation system is smaller, or that an appropriate shape is developed such that these alignment casings can be stacked closely, and thus only a small area of a patient's wound is needed during insertion of multiple bone screws.

The desirable bone screw fixation system has a positioning casing comprising a securing base and an alignment casing, both of which are integrally configured and a screw body passage is formed therethrough. A through hole is formed at the bottom of the securing base and along the screw body passage with its diameter smaller than that of the spherical head of the screw body. The wall of the securing base has two openings that are opposite to each other and open to the top of the securing base such that a first passage passing through the securing base is formed between the openings and laterally passes through the rod securing base. The alignment casing has a wall portion and a volume reduced portion. An elongated opening is formed on the wall portion and communicates with one of the openings. The volume reduced portion is a portion with part of the wall portion removed and thus receding from the outer surface of the securing base and a guide opening formed in the volume reduced portion which communicates with the other openings. An easy breaking portion is formed between the alignment casing and the positioning casing to facilitate removal of the alignment casing from the positioning casing. The easy breaking portion is selected from one of the following: (a) an annular notch; (b) a portion with a sharply reduced width or diameter of the alignment casing relative to that of the securing base; or (c) a series of small holes formed along the border between the alignment casing and the securing base. The positioning casing may further comprise a plurality of alignment openings at the wall portion of the alignment casing at the distal end from the securing base and a second notch slightly below the alignment openings and around the middle portion of the alignment casing such that the portion with the alignment openings can be broken.

Preferably, the entire wall of the volume reduced portion is removed so that the volume reduced portion recedes from the outer surface of the securing base; a receding area is a fictional area which corresponds to each of the cross sections of the volume reduced portion with its entire wall removed perpendicular to the screw body passage. The guide opening is formed due to the removal of the wall and the receding area of the alignment casing gradually increases from the end adjacent to the securing base toward the distal end far from the securing base. Further, the receding area of the cross-section at the distal end of the alignment casing is preferably equal to or more than half of the area of the cross-section of the top of the securing base. In addition, the securing base has a spherical pit at the bottom portion of the securing base; the inner surface right above the spherical pit is configured with a thread for fixation of a bone screw, and the positioning casing has a longitudinal length ranging from 85 to 165 mm.

In another aspect, the present disclosure describes a bone screw comprising the above positioning casing and a screw body. The screw body includes a screw rod and a spherical head connected to a top portion of the screw rod and is rotatably connected to a bottom portion of the positioning casing such that the positioning portion of the screw body is arranged in the spherical pit of the securing base. The spherical head has an outer diameter larger than the outer diameter of the screw rod and is configured with a joint notch and a non-slip texture. The joint notch conforms to the shape of a driving tool and the non-slip texture increases frictional force on the outer surface of the spherical head. The screw rod has a rod portion with an outer thread and a tip with an acute angle. When the bone screw is implanted into a vertebra, the alignment openings of the alignment casing remain above the skin.

In yet another aspect, the present disclosure describes a percutaneous minimally invasive pedicle fixation system comprising the above bone screw, a hook-rod and a set screw. The hook-rod includes a rod with a polygonal configuration at the rear end of the rod such that the installing angle and position of the hook-rod can be adjusted by means of the polygonal configuration. The set screw can be screwed with the thread of the inner surface right above the spherical pit to fix the hook-rod with the securing base. When the screw rod of the bone screw is implanted into a vertebra, the hook-rod can be inserted through a wound of skin, guided along the alignment casing to the bottom of the positioning casing, and can extend through the elongated opening and the guide opening of the alignment casing.

As a result, since the positioning casing is provided with an elongated opening and a guide opening so that a connecting means can pass therethrough and be guided along the alignment casing to the bottom of the positioning casing, the percutaneous minimally invasive pedicle fixation system of the present disclosure enables easier installation of the connecting means. Moreover, due to the positioning casing, the area of wounds can be reduced by closely stacking the positioning casings of multiple bone screws during operation. A connecting means can be a connecting rod, a hook-rod, or the like used for connecting the upper and lower vertebrae or connecting the pedicle with a vertebra to form a spine fixation system so as to resolve the problem of instability as a result of spine degeneration or related diseases. A connecting rod of titanium alloy with a diameter of about 5.5 mm can be used as a connecting means.

The above summary is not intended to describe each disclosed embodiment or every implementation of the present invention. The figures and the detailed description below particularly exemplify the illustrative embodiments.

DESCRIPTION OF THE DRAWINGS

FIGS. 5A-5E illustrates the installation of pedicle fixation system according to an embodiment of the present invention, wherein FIG. 5A shows a bone screw implanted and screwed into a vertebra; FIG. 5B shows a hook-rod guided along the alignment casing to the bottom of the positioning casing; FIG. 5C shows the hook-rod extended outwardly through the elongated opening and the guide opening of the alignment casing and is hooked to the pars interarticularis; FIG. 5D shows the hook-rod hooked to the pars interarticularis and secured to the securing base of the bone screw; and FIG. 5E shows the hook-rod secured to the securing base of the bone screw from another angle of view;

FIGS. 6A-6E illustrates the installation of bone screws according to another embodiment of the present invention, wherein FIG. 6A shows multiple bone screws implanted into the vertebrae; FIG. 6B shows the multiple bone screws of FIG. 6A further aligned by alignment fixtures; FIG. 6C shows the multiple bone screws of FIG. 6B temporarily secured by the alignment fixture and a connecting rod positioned in the securing base; FIG. 6D shows that the connecting rod has been secured to the securing bases of multiple bone screws and that the alignment casings of the positioning casings have all been removed; and FIG. 6E shows that the connecting rod is secured to the securing bases of multiple bone screws; and FIGS. 7A and 7B illustrate the installation of bone screws according to another embodiment of the present invention, wherein FIG. 7A shows that multiple bone screws are implanted into the vertebrae through the same small wound of skin; and FIG. 7B shows the upper portions of the positioning casings of two bone screws remaining above the skin and stacked together.

DETAILED DESCRIPTION OF THE INVENTION

In the following description, reference is made to the accompanying drawings. It is to be understood that other embodiments are contemplated and may be made without departing from the scope or spirit of the present disclosure. The following detailed description is to better illustrate the invention instead of limiting the invention to the following description.

Figure 1:
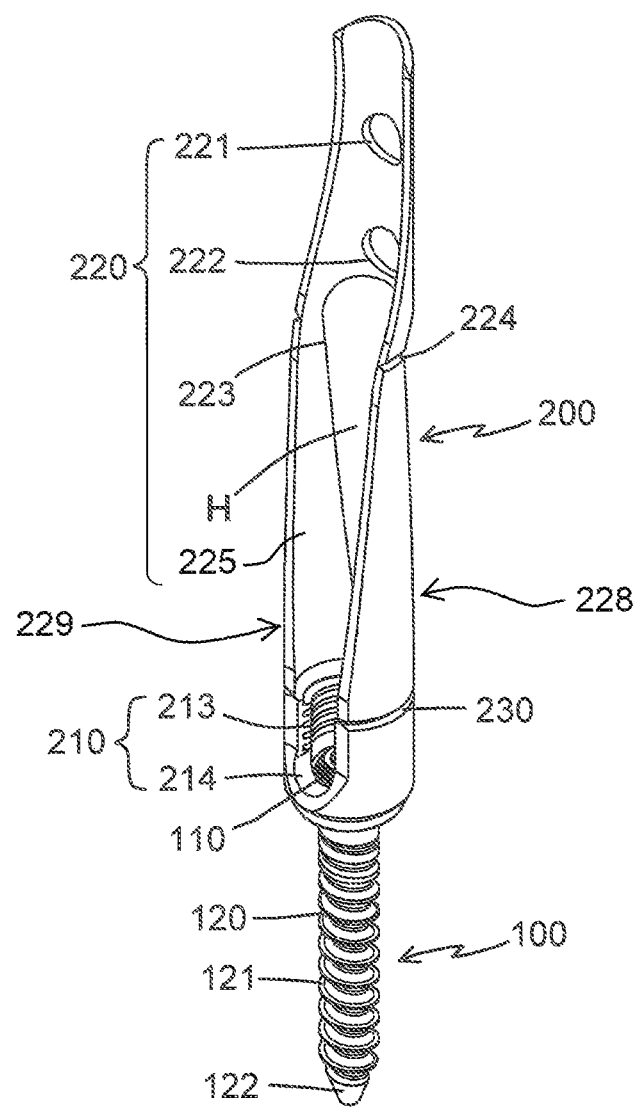
FIG. 1 illustrates a perspective view of the bone screw according to an embodiment of the present invention.
Figure 2:
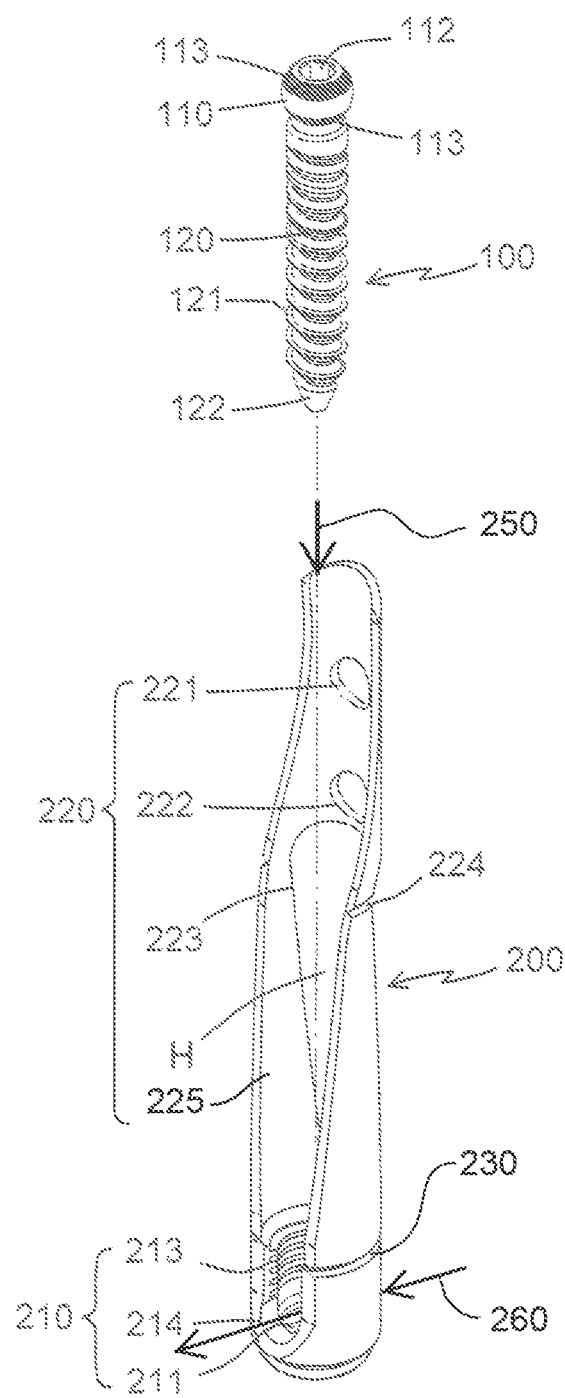
FIG. 2 illustrates a perspective view of the bone screw in a disassembled state according to an embodiment of the present invention.
Figure 3:
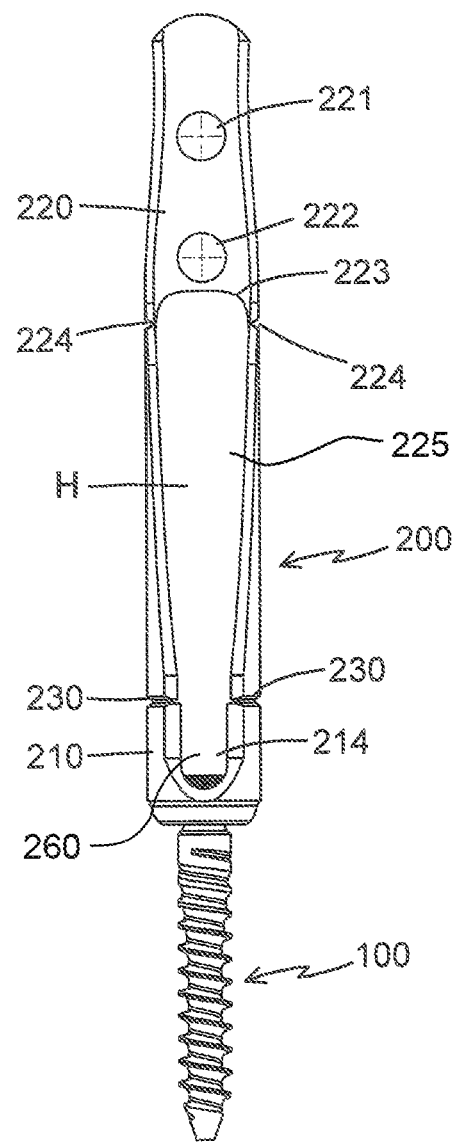
FIG. 3 illustrates a side view of the bone screw in an assembled state according to an embodiment of the present invention.

As shown in FIGS. 1-3, a bone screw comprises a positioning casing 200 and a screw body 100. The screw body 100 includes a screw rod 120 and a spherical head 110; the screw body 100 is able to pass through the alignment casing 220 and rotatably connect to a bottom portion of the positioning casing 200. The spherical head 110 has an outer diameter larger than the outer diameter of the screw rod 120. The positioning casing 200 includes a securing base 210 and an alignment casing 220, both of which are integrally formed, and a screw body passage 250 formed therethrough. The bottom of the securing base 210 is formed with a through hole along the screw body passage 250 with its diameter smaller than that of the spherical head 110 of the screw body 100. The wall of the securing base 210 has two openings 214 that are opposite to each other and open to the top of the securing base 210 such that a first passage 260 passing through the securing base 210 is formed between the openings 214 and laterally passes through the securing base 210. The securing base 210 further includes a spherical pit 211 at the bottom portion of the securing base 210 and the inner surface right above the spherical pit 211 is configured with a thread 213.

The alignment casing 220 has a wall portion 228 and a volume reduced portion 229. The wall portion 228 is formed with the wall, an elongated opening 223 communicating with one of the openings 214, and a plurality of alignment openings 221, 222 at the distal end far from the securing base 210. The alignment casing 220 further has a second notch 224 slightly below the alignment openings 221, 222 and around the alignment casing 220 such that the portion with the alignment openings 221, 222 can be easily broken. The volume reduced portion 229 is a portion with part of the wall portion 228 removed to recede from the outer surface of the securing base 210. A guide opening 225 formed in the volume reduced portion 229 communicates with the other of the openings 214. Another preferred embodiment is that the entire wall of the volume reduced portion 229 is removed, and thus the volume reduced portion 229 forms the guide opening 225. A receding area is a fictional area which corresponds to each of the cross sections of the volume reduced portion 229 with its entire wall removed perpendicular to the screw body passage 250. In a preferable embodiment, the wall portion 228 includes two walls symmetrical about the longitudinal center axis of the screw body passage 250; the receding area of the cross-section of the alignment casing 220 gradually increases from the end adjacent to the securing base 210 toward the end distal from the securing base 210 and is more than half of the area of the cross-section of the top of the securing base 210 at the distal end of the alignment casing 220. The positioning casing 200 preferably has a longitudinal length ranging from 85 to 165 mm.

Moreover, the positioning casing 200 has an easy breaking portion to facilitate the removal of the alignment casing 220. For example, an annular notch 230 is formed between the alignment casing 220 and the securing casing 210 so that the alignment casing 220 can be easily removed from the positioning casing (200) by breaking it. Another example is that the easy breaking portion is a portion with a sharply reduced width or diameter of the alignment casing 220 relative to that of the securing base 210. The easy breaking portion can also be a series of small holes formed along the border between the alignment casing 220 and the securing base 210.

In FIG. 2, the bone screw is in a disassembled state. The screw body 100 includes the screw rod 120 and the spherical head 110 connected to a top portion of the screw rod 120. The spherical head 110 has a joint notch 112 that conforms to the shape of a driving tool, and has a non-slip texture 113 for increasing frictional force on the outer surface of the spherical head 110. The screw rod 120 has a rod portion with an outer thread 121 and a tip 122 formed with an acute angle at the end of the rod portion.

In an assembled state of the bone screw, as shown in FIGS. 1 and 3, the screw body 100 is rotatably connected to a bottom portion of the positioning casing 200 such that the spherical head 110 of the screw body 100 is arranged in the spherical pit 211 (shown in FIG. 2) of the securing base 210.

Figure 4:
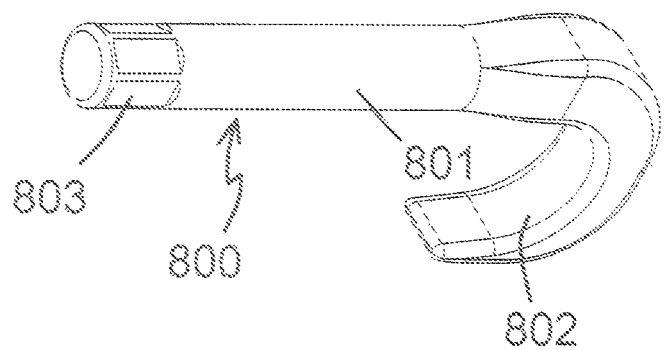
FIG. 4 illustrates a perspective view of the hook-rod according to an embodiment of the present invention.
Figure 5A:
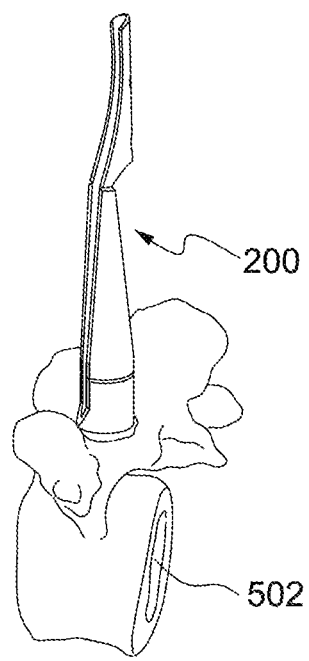
Figure 5B:
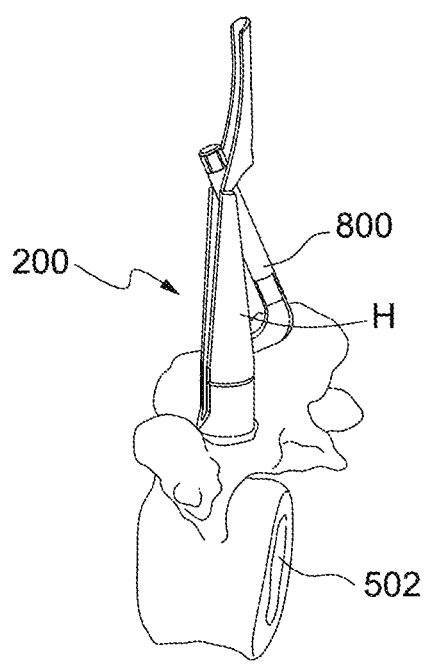
Figure 5C:
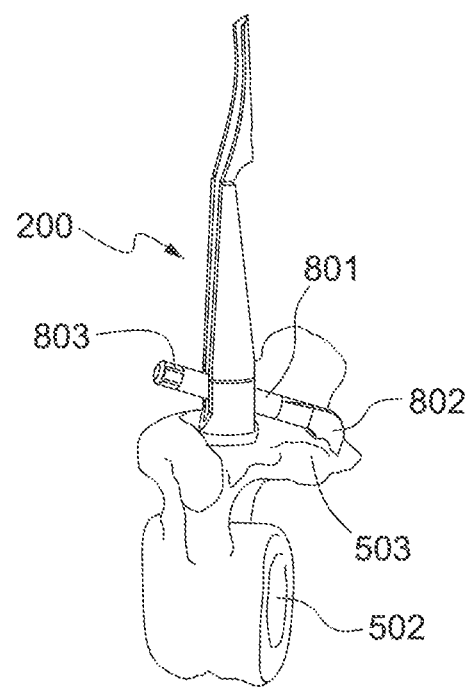
Figure 5D:
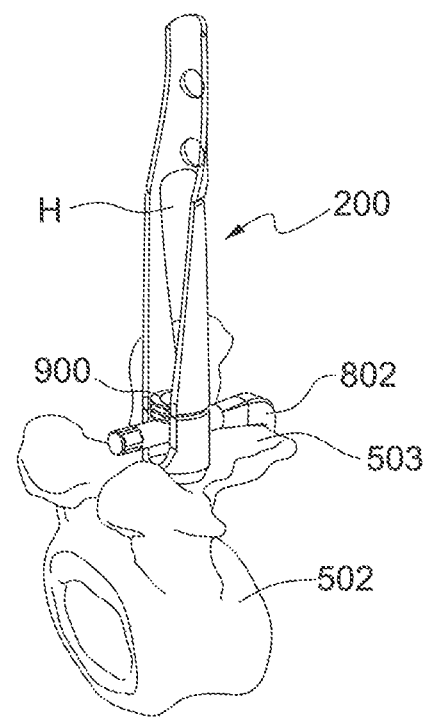

FIGS. 5A-5E show a percutaneous minimally invasive pedicle fixation system. The percutaneous minimally invasive pedicle fixation system comprises a bone screw, as described above, a hook-rod 800, and a set screw 900. The pedicles discussed herein may have defects or in a condition of spondylolysis. The hook-rod 800, as shown in FIG. 4, has a hook portion 802, a rod 801 and a polygonal configuration 803 at the rear end of the rod 801. The polygonal configuration 803 facilitates adjustment of the installing angle and position of the hook-rod 800 by tools. The set screw 900, as shown in FIG. 5D, can be screwed along the thread 213 of the inner surface of the positioning casing 200 right above the spherical pit 211 to fix the hook-rod 800 with the securing base 210.

Figure 5E:
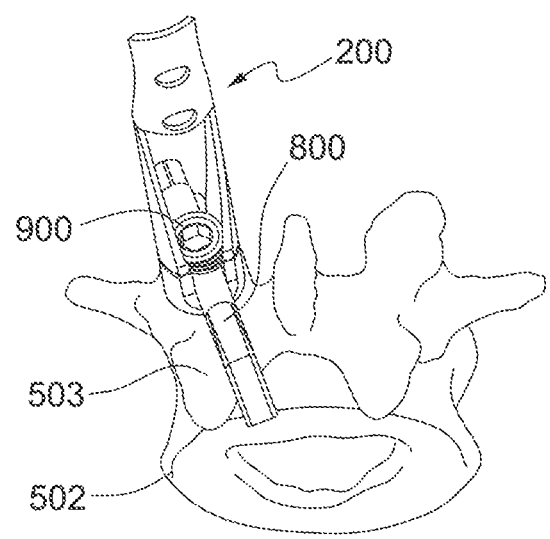

The following describes an example of percutaneous minimally invasive pedicle fixation surgery while referring to FIGS. 5A-5E. First, the front end of a driving tool (not shown) abuts against the joint notch 112 of the spherical head 110 of the screw body 100 and enters into the positioning casing 200 for rotating the screw body 100 and implanting the screw rod 120 into the vertebra 502, as shown in FIG. 5A. After the screw rod 120 is screwed into the bone, a set screw 900 is screwed into the spherical pit 211 (shown in FIG. 2) of the securing base 210 along the thread 213 to prevent the screw body 100 from being backward, and a portion of the alignment casing 220 is still above the wound of skin. Subsequently, as shown in FIGS. 5B-5C, the hook-rod 800 is inserted into and guided along the positioning casing 200 to the bottom of the positioning casing 200. The hook-rod 800 moves along the elongated opening 223 and the guide opening 225 of the alignment casing 220 and the installing angle and position of the hook-rod 800 can be adjusted by means of the polygonal configuration 803 with tools. Thus, the hook portion 802 of the hook-rod 800 can be accurately fixed with the pars interarticularis 503 at a predetermined position. Further, as shown in FIGS. 5D-5E, the set screw 900 is screwed along the thread 213 of the inner surface right above the spherical pit 211 to fix the hook-rod 800 to the securing base 210. Lastly, an external force is exerted to the annular notch 230 of the positioning casing 200 to break the annular notch 230. As a result, the alignment casing 220 can be separated and removed from the securing base 210 and taken out of the human body.

According to the above descriptions, the percutaneous minimally invasive pedicle fixation system of the present invention can be used to secure the pars interarticularis 503, increase the stability of vertebrae, and prevent the pars interarticularis 503 from aggravating or turning into spondylolysis or spondylolisthesis.

Figure 6A:
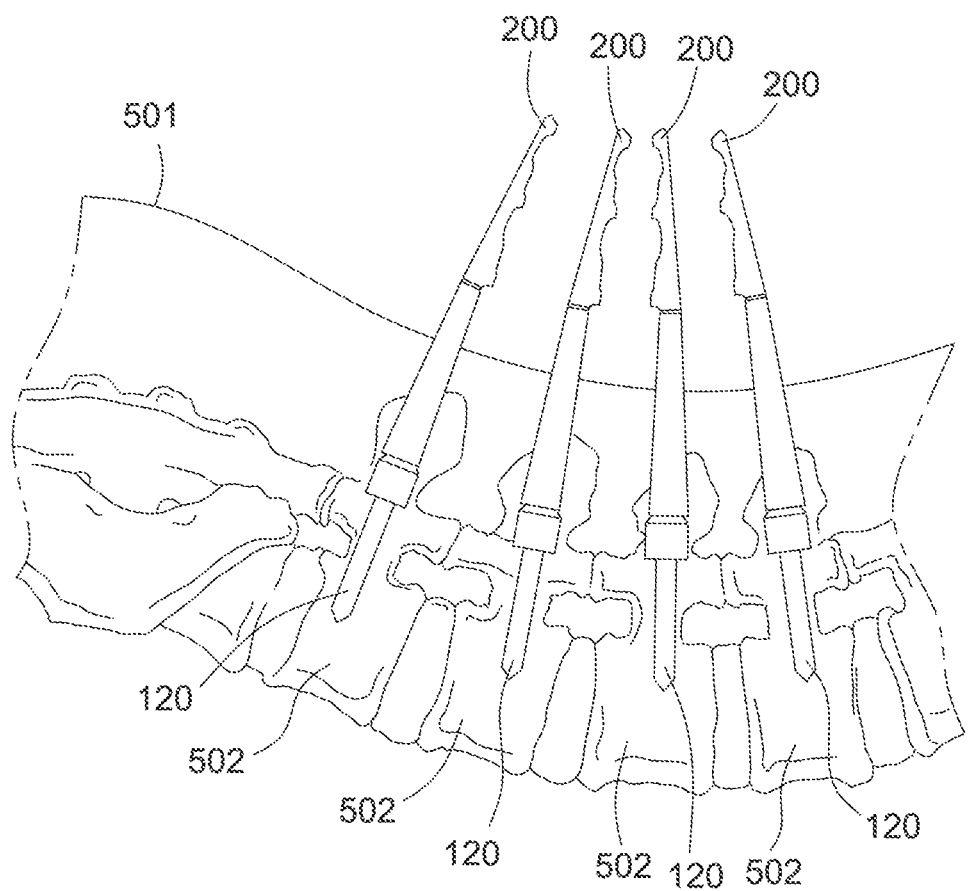
Figure 6B:
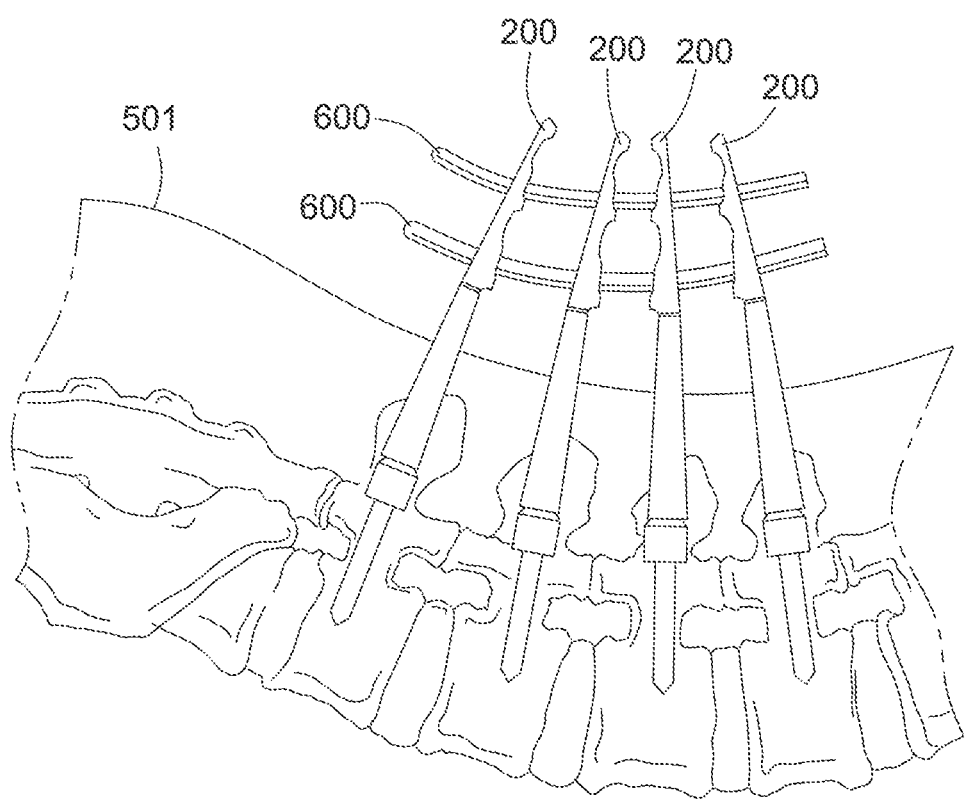

The following describes an example of installation of a fixation system for multiple vertebrae in a minimally invasive surgery while referring to FIGS. 6A-6E. First, a bone screw 200 is placed into the wound of skin 510 as shown in FIG. 6A. A driving tool (not shown) abuts against the joint notch 112 of the spherical head 110 of the screw body 100 and enters into the positioning casing 200 for rotating and implanting the screw rod 120 into the vertebra 502. After the bone screw is implanted into the vertebra 502, since the positioning casing 200 has a length of about 100 mm and since the vertebrae are generally at a depth of about 35 to 50 mm below the skin, a large portion of the alignment casing 220 of the positioning casing 200 remains above the skin. Particularly, the alignment openings 221, 222 of the wall portion 228 remain above the skin such that the bone screw can be aligned by an alignment fixture 600 from above the skin. As shown in FIGS. 6A and 6B, four bone screws are respectively implanted into four vertebrae, and two alignment fixtures 600 pass through the alignment openings 221, 222 of the alignment casings 220. After the angles and positions of the bone screws are adjusted, the alignment openings 221, 222 are properly positioned to conform to the curve of the alignment fixtures 600. The alignment fixtures have a curve approximately equal to that of the spine to which the fixation system is to be installed. That is, after alignment, the positions of the bone screws approximately conform to the curve of the spine.

Figure 6C:
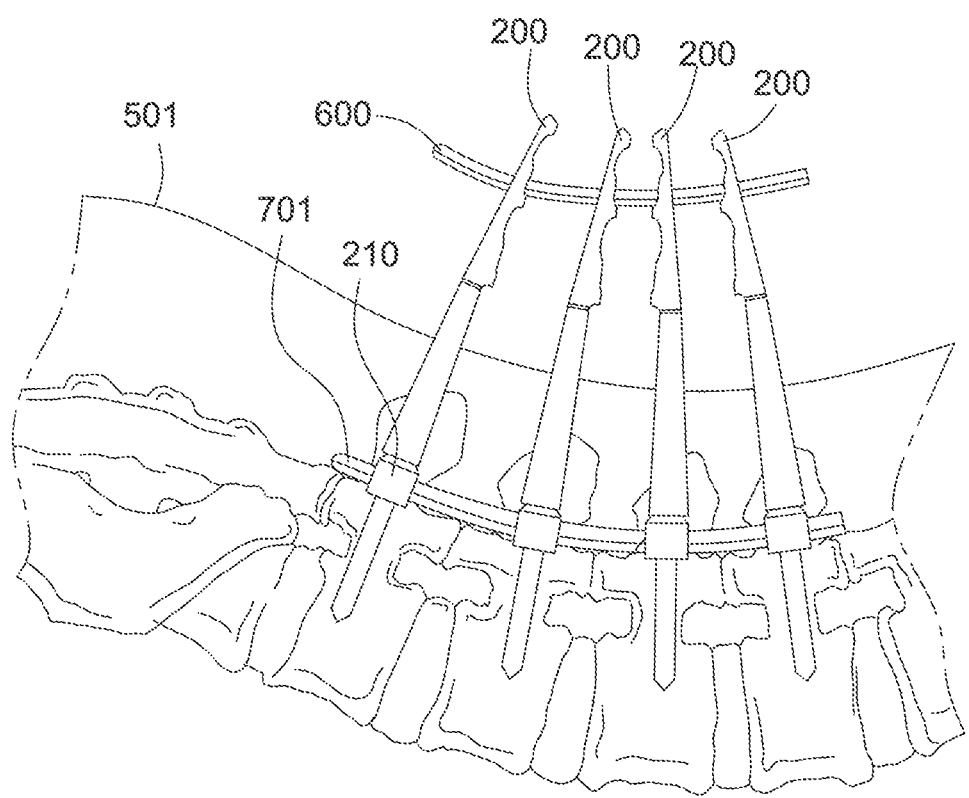

As shown in FIG. 6C, the lower one of the alignment features 600 is removed to facilitate the insertion of a connecting rod 701. The connecting rod 701 is disposed in the openings 214 of the securing bases 210 and fixed to the securing bases 210 by the set screws 900, which are screwed along the thread 213 of the inner surface right above the spherical pit 211. Since the connecting rod 701 has a similar curve to that of the alignment fixtures 600, it can be accurately positioned on the securing bases 210 of the positioning casings 200. It is also applicable to remove both of the alignment features 600 as well as the portion of the alignment casing above the second notch 224 by exerting an external force since the second notch 224 facilitates the removal process.

Figure 6D:
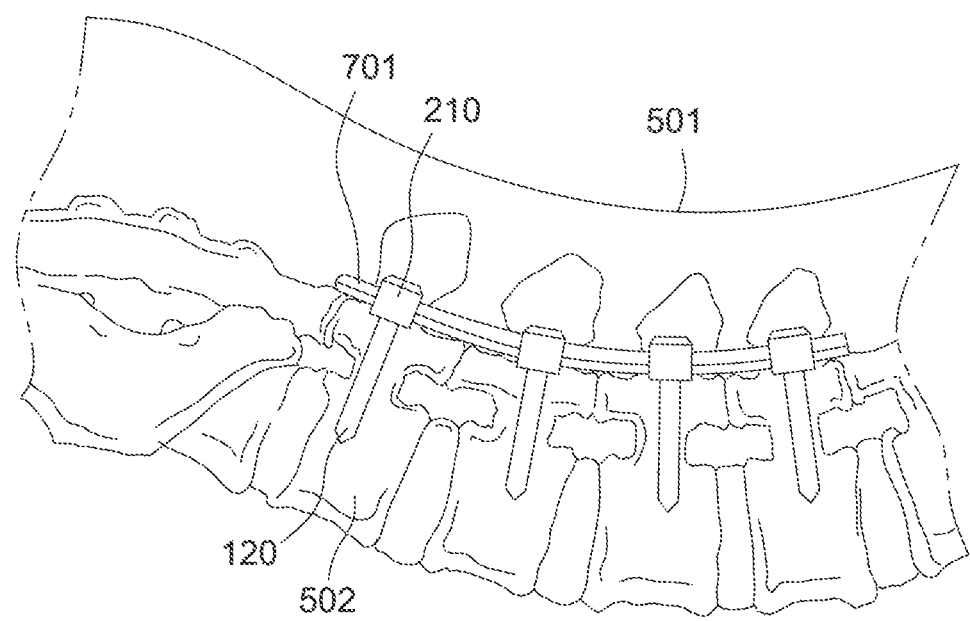
Figure 6E:
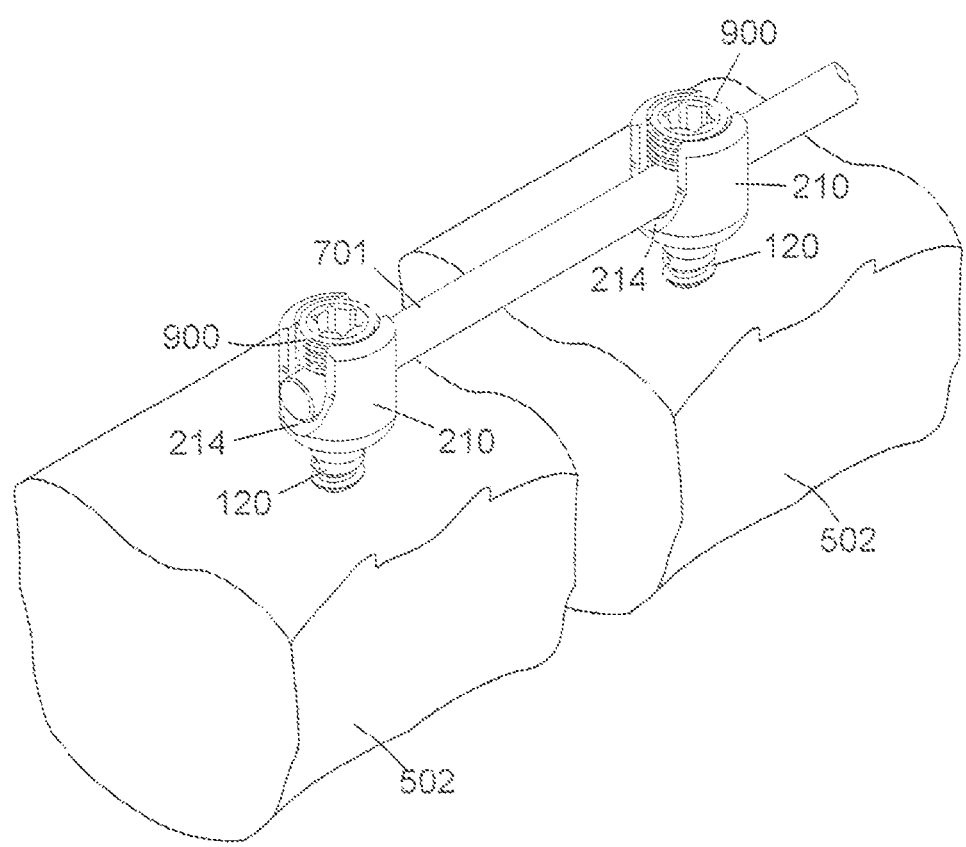

The last step is to remove the alignment fixtures 600 and exert an external force by a separation tool (not shown) or by hand to remove the positioning casings 210; due to the annular notches 230 of the positioning casings, the alignment casings 220 can be easily broken and removed. Thus, as shown in FIGS. 6D and 6E, the alignment casings 220 of the positioning casings 200 have been separated from the securing bases 210 and removed from the human body. The installation of a fixation system for multiple vertebrae in a minimally invasive surgery is accomplished.

Figure 7A:
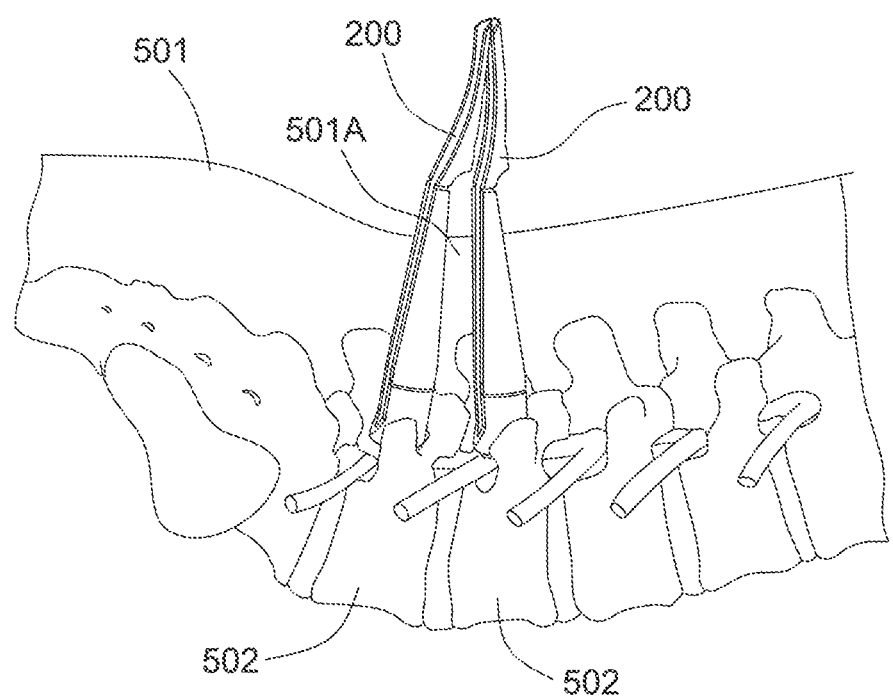
Figure 7B:
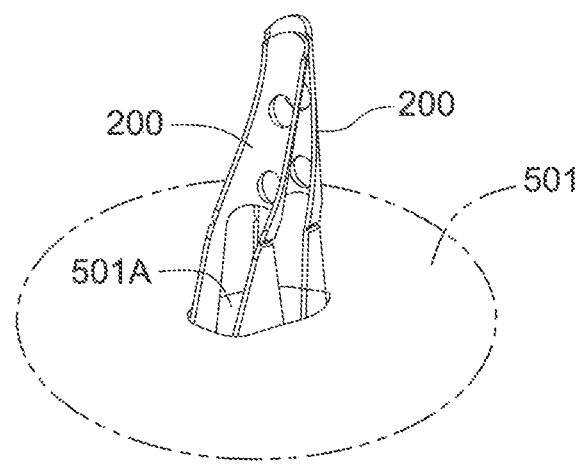

In another embodiment of the present invention, as shown in FIGS. 7A and 7B, two or more bone screws are implanted neighboring one another, but only a small area of a patient's wound is needed during insertion of multiple bone screws. Due to the volume reduced portion 229 of the positioning casing 200, the wall portion of one positioning casing 200 can be partly received in the volume reduced portion of another positioning casing 200 during installation of multiple bone screws. That is, one alignment casing 220 with the volume reduced portion 229 are stacked onto the other. As a result, the area of the wound 501A, and thus the time needed for healing and recovery, can be considerably reduced.

Although the present invention has been described in relation to particular embodiments thereof, many other variations and modifications and other uses may become apparent to those skilled in the art. It is preferred, therefore, that the present invention be limited not by the specific descriptions herein, but only by the appended claims.

What is claimed is:

1. A positioning casing of a bone screw used to fit a screw body, comprising a securing base and an alignment casing, both of which are integrally configured and a screw body passage is formed therethrough, wherein:
a through hole is formed at a bottom of the securing base and along the screw body passage with its diameter smaller than that of a spherical head of the screw body;
a wall of the securing base has two openings opposite to each other and open to a top of the securing base such that a first passage passing through the securing base is formed between the openings and laterally passes through the securing base;
the alignment casing has a wall portion and a volume reduced portion; an elongated opening is formed on the wall portion and communicates with one of the openings; said volume reduced portion is a portion with part of the wall portion removed and thus receding from an outer surface of the securing base and a guide opening formed in the volume reduced portion which communicates with another one of the openings;
a first easy breaking portion is formed between the alignment casing and the securing base to facilitate the removal of the alignment casing from the securing base;
a plurality of alignment openings are formed at the wall portion of the alignment casing at a distal end from the securing base;
in the volume reduced portion, the entire wall is removed to form the guide opening, and the distal end of the alignment casing relative to the screw body passage has a receding area that gradually increases from an end adjacent to the securing base toward the distal end far from the securing base; and
the wall portion includes two walls symmetrical about a longitudinal center axis of the screw body passage, and the receding area of the cross-section in the volume reduced portion at the distal end of the alignment casing is equal to or more than half of an area of the cross-section of the top of the securing base.

2. The positioning casing of a bone screw according claim 1, wherein a second notch is formed slightly below the alignment openings and around the middle portion of the alignment casing such that the portion with the alignment openings can be broken.

3. The positioning casing of a bone screw according to claim 1, wherein the easy breaking portion is selected from one of the following: (a) an annular notch; (b) a portion with a sharply reduced width or diameter of the alignment casing relative to that of the securing base; or (c) a series of small holes formed along the border between the alignment casing and the securing base.

4. The positioning casing of a bone screw according to claim 1, wherein the securing base further has a spherical pit at the bottom portion of the securing base and the inner surface right above the spherical pit is configured with a thread.

5. The positioning casing of a bone screw according to claim 1, wherein the positioning casing has a longitudinal length ranging from 85 mm to 165 mm.

6. A bone screw, comprising:
a positioning casing according to claim 1; and
a screw body including a screw rod and a spherical head connected to a top portion of the screw rod, wherein:
the screw body is rotatably connected to a bottom portion of the positioning casing such that the positioning portion of the screw body is arranged in a spherical pit at the bottom portion of the securing base;
an other diameter of the spherical head is larger than an outer diameter of the screw rod;
the spherical head is configured with a joint notch, which conforms to the shape of a driving tool and with a non-slip texture for increasing frictional force on the outer surface of the spherical head; and
the screw rod has a rod portion with an outer thread and a tip with an acute angle.

7. The bone screw according to claim 6, wherein the plurality of alignment opening which are formed at the wall portion of the alignment casing at the distal end from the securing base remain above the skin when the bone screw is implanted into a vertebra.

8. A percutaneous minimally invasive pedicle fixation system, comprising:
a bone screw according to claim 7;
a hook-rod including a rod with a polygonal configuration at the rear end of the rod such that the installing angle and position of the hook-rod can be adjusted by means of the polygonal configuration; and
a set screw that can be screwed with a thread of the inner surface right above the spherical pit to fix the hook-rod with the securing base, wherein:
when the screw rod of the bone screw is implanted into a vertebra, the hook-rod can be inserted through a wound of skin, guided along the alignment casing to the bottom of the positioning casing, and can extend through the elongated opening and the guide opening of the alignment casing.

* * * * *